(12) United States Patent
Burns, Jr. et al.

(10) Patent No.: US 6,328,723 B1
(45) Date of Patent: Dec. 11, 2001

(54) ABSORBENT ARTICLE COMPRISING MICROPOROUS FILM

(75) Inventors: John Glasgow Burns, Jr., Kobe (JP); Chiun-hsien Chang, Cincinnati, OH (US); Kazushige Kishida, Kobe (JP); Guido Bonelli, Pascara via Colle Innamorati (IT); Tsunetoshi Miura, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/623,814

(22) PCT Filed: Oct. 29, 1998

(86) PCT No.: PCT/US98/23029

§ 371 Date: Sep. 8, 2000

§ 102(e) Date: Sep. 8, 2000

(87) PCT Pub. No.: WO99/45871

PCT Pub. Date: Sep. 16, 1999

(30) Foreign Application Priority Data

| Mar. 10, 1998 | (WO) | PCT/US98/04650 |
| Mar. 10, 1998 | (WO) | PCT/US98/04651 |
| Mar. 10, 1998 | (WO) | PCT/US98/04673 |

(51) Int. Cl.$^7$ .................................................. A61F 13/15
(52) U.S. Cl. ..................... 604/385.22; 604/370; 604/372
(58) Field of Search ........................ 604/385.22, 385.01, 604/385.03, 385.04, 385.23, 385.24, 367, 370, 372; 428/454, 500

(56) References Cited

U.S. PATENT DOCUMENTS

| 4,116,892 | 9/1978 | Schwarz | 521/62 |
| 4,153,751 | 5/1979 | Schwarz | 428/304 |
| 4,166,464 | * 9/1979 | Korpman | 128/287 |
| 4,289,831 | 9/1981 | Last | 428/515 |
| 4,921,653 | * 5/1990 | Aoyama et al. | 264/41 |
| 4,923,650 | 5/1990 | Antoon, Jr. et al. | 264/41 |
| 5,389,094 | 2/1995 | Lavash et al. | 604/385.2 |
| 5,704,930 | 1/1998 | Lavash et al. | 604/385.2 |

FOREIGN PATENT DOCUMENTS

| 05-230252 | 9/1993 | (JP) . |
| 06-062794 | 8/1994 | (JP) . |
| 07-231913 | 9/1995 | (JP) . |
| 2637389 | 9/1996 | (JP) . |
| 08-300436 | 11/1996 | (JP) . |
| 08-300499 | 11/1996 | (JP) . |
| 08-300500 | 11/1996 | (JP) . |
| WO 96/12462 | 5/1996 | (WO) . |
| WO 97/12576 | 4/1997 | (WO) . |

* cited by examiner

*Primary Examiner*—Dennis Ruhl
*Assistant Examiner*—Jamisue Webb
(74) *Attorney, Agent, or Firm*—Caroline Wei-Berk; Ken K. Patel; Steven W. Miller

(57) ABSTRACT

An absorbent article having a breathable microporous film is disclosed. The breathable microporous film is made by stretching a mixture of a thermoplastic resin and inorganic fillers at least in one direction. At least a part of the breathable microporous film is deformed such that Z number specified by equation (1) is 3.0 or above, wherein MS: average material strain at break of breathable microporous film; AS: average applied strain for deformation; N: neck down prevention coefficient; σMS: standard deviation of material strain at break; σAS: standard deviation of applied strain.

10 Claims, 7 Drawing Sheets

ABSORBENT ARTICLE COMPRISING MICROPOROUS FILM

FIELD

The present invention relates to an absorbent article comprising a microporous film.

BACKGROUND

A microporous film having breathability is well known and used for various consumer products such as packaging film and absorbent articles. There are prior art which are directed to improvement of such a microporous film, such as U.S. Pat. No. 4,923,650 published on May 8, 1990. JP Patent publication 93/230252-A published on Sep. 7, 1993. JP Patent publication 96/225680-A published on Sep. 3, 1996. JP Patent publication 94/62794-B published on Aug. 17, 1994, JP Patent publication 95/231913-A published on Sep. 5, 1995. JP Patent publication 96/300436-A published on Nov. 19, 1996. JP Patent publication 96/300498-A published on Nov. 19, 1996. JP Patent publication 96/300499-A published on Nov. 19, 1996. JP Patent publication 96/300500-A published on Nov. 19, 1996, and JP Patent publication 87/167332-A published on Jul. 23, 1987. The microporous film described in these publications worked quite well as a backsheet of an absorbent article which requires breathability and liquid impermeability. There are also publications which are directed to a process for making a microporous film and the microporous film made by the process, such as U.S. Pat. No. 4,116.892 published on Sep. 26, 1978, U.S. Pat. No. 4,153,751 published on May 8, 1979. and U.S. Pat. No. 4,289.831 published on Sep. 15, 1981. These publication disclose processes using a process of stretching a material to make a microporous film. However, none of the publication disclose a microporous film having extensibility or a process to make a microporous film having extensibility so that a part of a microporous film is extensible. These publications are directed to a technology to make non-microporous film microporous, but not a technology to make a microporous film extensible.

Absorbent articles such as a sanitary napkin having a portion of extensibility are disclosed in prior art, such as PCT publication WO 97/12576 published on Apr. 10, 1997, PCT publication WO 96/12462 published on May 1, 1996, U.S. Pat. No. 5,389.094 published on Feb. 14, 1995 and U.S. Pat. No. 5,704,930 published on Jan. 6, 1998. In these disclosures, the flaps of the sanitary napkin are provided extensibility for relieving the stresses that develop in the flaps when the flaps are folded down and under a wearer's undergarment. The extensibility can be provided by a number of different processes. For example, the extensibility on the flaps can be provided by mechanically straining, corrugating, "ring-rolling", heating and deforming, subjecting portions of the flaps to compression between mating plates, and the like. These processes include the process of applying a strain to a material to mechanically and permanently deform the material. Extensibility on the material is provided by remaining permanent deformation on the material. Therefore, a degree of extensibility is determined by a degree of an applied strain. The more extensibility requires, the higher strain is applied to the material.

As described above, microporous films are commonly used for a breathable backsheet of an absorbent article. Microporous films typically comprise a blend of a thermoplastic polymer and an inorganic filler such as calcium carbonate. The blend undergoes pore formation upon stretching as the inorganic filler separates from the polymer due to stress concentration. The formation of micropores permits the film to be breathable allowing the passage of vapor through the micropores while retarding the passage of liquid. While microporous films have good breathability, microporous films have lower "strain at break" than an ordinary non-microporous film. Therefore, if microporous films are subjected to high strain beyond the strain at break of the microporous film for deformation to obtain extensibility of the microporous film, such high strain causes many visible pin holes in the area where the strain is applied.

Based on the foregoing, there is a need of improvement for an absorbent article comprising a microporous film. None of the existing art provides all of the advantages and benefits of the present invention.

SUMMARY

The present invention relates to an absorbent article having a breathable microporous film. The breathable microporous film is made by stretching a mixture of a thermoplastic resin and inorganic fillers at least in one direction. At least a part of the breathable microporous film is deformed such that Z number specified by a following equation is 3.0 or above.

$$Z = \frac{N \cdot MS - AS}{\sqrt{\sigma_{AS}^2 + \sigma_{MS}^2}}$$

wherein
MS average material strain at break of breathable microporous film
AS: average applied strain for deformation
N: neck down prevention coefficient
$\sigma_{MS}$ standard deviation of material strain at break
$\sigma_{AS}$ standard deviation of applied strain The present invention further relates to an absorbent article having a breathable microporous film, the breathable microporous film having extensibility. The breathable microporous film is made by stretching a mixture of a thermoplastic resin and inorganic fillers at least in one direction. At least a part of the breathable microporous film is imparted a predetermined extensibility by being deformed such that Z number specified by a following equation is 3.0 or above.

$$Z = \frac{N \cdot MS - AS}{\sqrt{\sigma_{AS}^2 + \sigma_{MS}^2}}$$

wherein
MS: average material strain at break of breathable microporous film
AS: average applied strain to obtain a predetermined extensibility
N: neck down prevention coefficient
$\sigma_{MS}$: standard deviation of material strain at break
$\sigma_{AS}$: standard deviation of applied strain The present invention further relates to an absorbent article having a breathable microporous film, the breathable microporous film having extensibility. The breathable microporous film is made by stretching a mixture of a thermoplastic resin and inorganic fillers at least in one direction. The breathable microporous film has a basis weight of 30 g/m$^2$ or above. At least a part of the breathable microporous film is imparted a predetermined extensibility by being deformed- The predetermined extensibility is from 50% to 100%.

The present invention further relates to an absorbent article having a breathable microporous film, the breathable microporous film having extensibility. The breathable microporous film is made by stretching a mixture of a thermoplastic resin and inorganic fillers at least in one direction. The breathable microporous film includes the inorganic fillers with particle size of 20 mm or less. At least a part of the breathable microporous film is imparted a predetermined extensibility by being deformed. The predetermined extensibility is from 50% to 100%.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION OF THE INVENTION

All cited references are incorporated herein by reference in their entireties. Citation of any reference is not an admission regarding any determination as to its availability as prior art to the claimed invention.

"Comprising" means that other steps and other elements which do not affect the end result can be added. This term encompasses the terms "consisting of" and "consisting essentially of".

Figure 1:
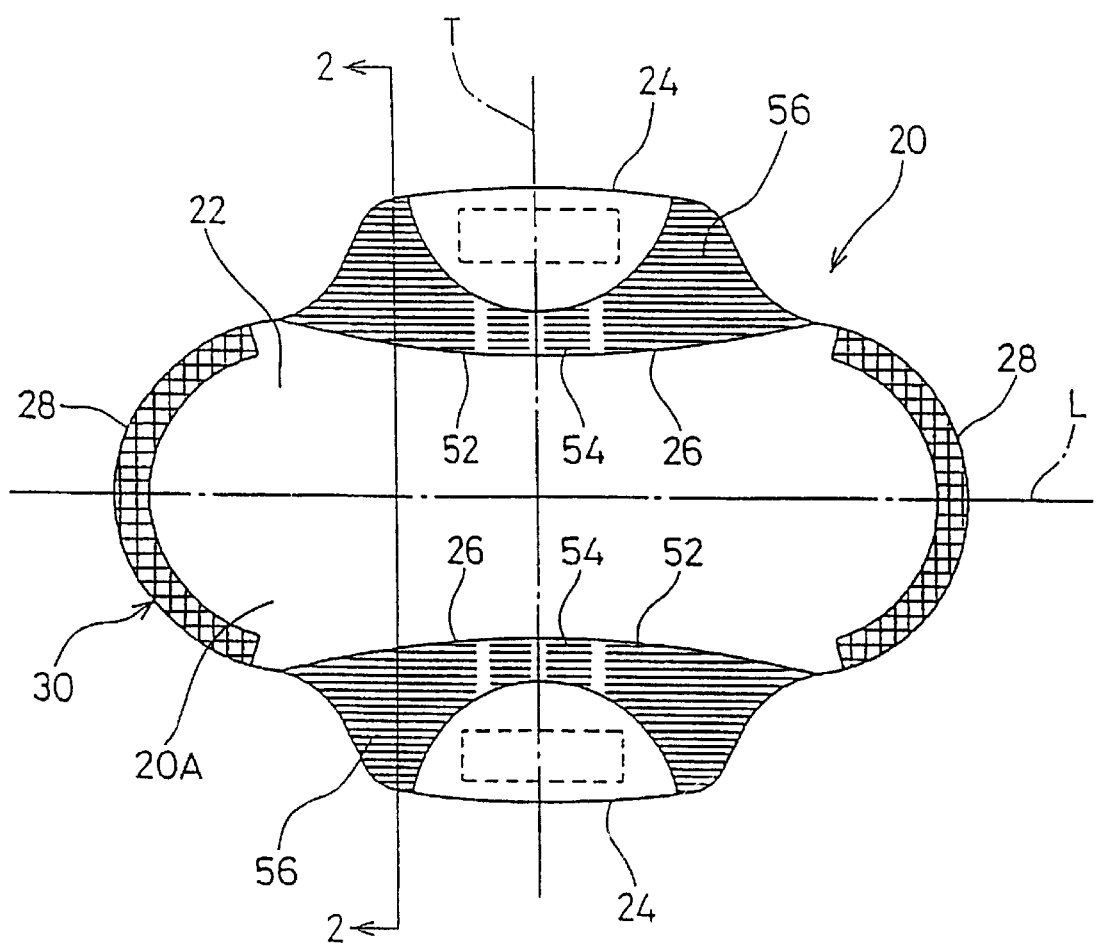
FIG. 1 is a top plan view of a preferred sanitary napkin embodiment of the present invention.

A preferred embodiment of a sanitary napkin 20 of the present invention is shown in FIG. 1. As shown in FIG. 1, the sanitary napkin 20 basically comprises an absorbent means (or "main body portion") 22, and two flaps 24. The sanitary napkin 20 has two surfaces, a body-contacting surface or "body surface" 20A and a garment surface 20B. The sanitary napkin 20 is shown in FIG. 1 as viewed from its body surface 20A. The body surface 20A is intended to be worn adjacent to the wearer's body. The garment surface 20B is intended to be placed adjacent to the wearer's undergarments when the sanitary napkin 20 is worn. The sanitary napkin 20 has two centerlines, a principal longitudinal centerline L and a principal transverse centerline T.

FIG. 1 shows that the main body portion 22 of the sanitary napkin 20 comprises the portion of the sanitary napkin without the flaps 24. The main body portion 22 has two spaced apart longitudinal edges 26, two spaced apart transverse or end edges (or "ends") 28, which together form the periphery 30 of the main body portion. The main body portion 22 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn preferably has a caliper of less than about 3 millimeters. The embodiment of the sanitary napkin 20 shown in the drawings is intended to be an example of a sanitary napkin of an intermediate thickness. The main body portion 22 of the sanitary napkin 20 may also be relatively flexible, so that it is comfortable for the wearer. It should be understood that the sanitary napkin shown is merely one embodiment, and that the present invention is not limited to absorbent articles of the type or having the specific configurations shown in the drawings.

Figure 2:
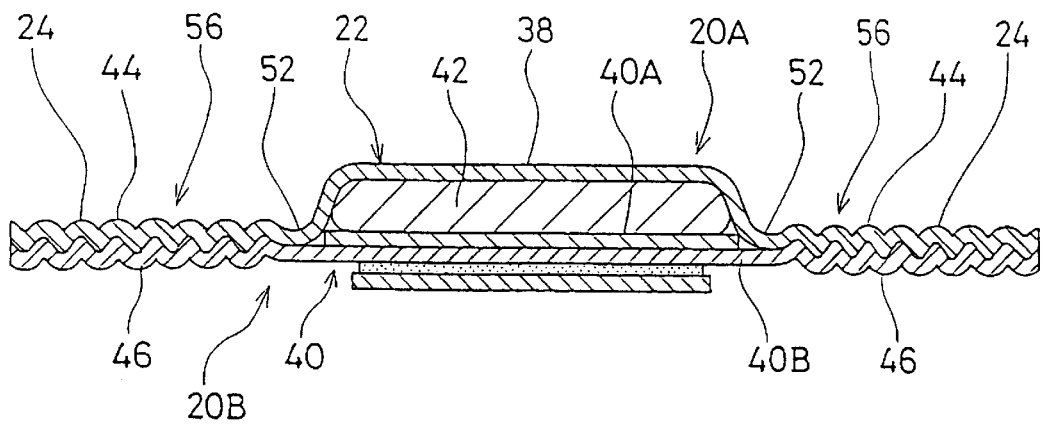
FIG. 2 is a lateral cross-sectional view taken along line 2—2 of FIG. 1 through the corner region of the flaps of the sanitary napkin.

FIG. 2 shows the individual components of the main body portion 22 of the sanitary napkin 20 of the present invention. The main body portion 22 of the sanitary napkin 20 preferably comprises at least three primary components. These include a liquid pervious topsheet 38 typically provided by a liquid permeable substrate of fibrous such as nonwoven or film like structure such as apertured formed films, a liquid impervious backsheet 40 preferably provided by a liquid impermeable, but breathable substrate, and an absorbent core 42 positioned between the topsheet 38 and the backsheet 40. The backsheet 40 comprises two layers; a first layer comprising a gas permeable apertured formed film layer 40A and a second layer comprising a breathable microporous film layer 40B.

The topsheet, the backsheet, and the absorbent core may be assembled in a variety of configurations known in the art (including layered or "sandwich" configurations and wrapped or "tube" configurations). FIGS. 1 and 2 show a preferred embodiment of the sanitary napkin 20 assembled in a sandwich construction in which the topsheet 38 and the breathable microporous film 40B have length and width dimensions generally larger than those of the absorbent core 42. The topsheet 38 and the breathable microporous film 40B extend beyond the edges of the absorbent core 42 to form portions of the periphery 30. The apertured formed film 40A of the backsheet has the approximately same shape as the absorbent core 42 to cover at least the region where the absorbent core 42 lies as shown in FIG. 2. Alternatively, it may have a little bigger shape than the absorbent core 42, or may have the same shape as the main body portion 22 of the sanitary napkin 20. In any case, preferably, the apertured formed film 40A does not extend into the flaps 24 as shown in FIG. 2. Alternatively, the apertured formed film 40A may extend into the flaps 24 so that the apertured formed film constitutes a part of the flaps 24.

The topsheet 38 is preferably joined to the body-facing side of the absorbent core 42 and the backsheet 40 (i.e., the apertured formed film 40A) is preferably joined to the garment-facing side of the absorbent core 42. The topsheet 38 and the apertured formed film 40A can be joined to the absorbent core 42 in any suitable manner known in the art for this purpose, such as by an open pattern of adhesives. The portions of the topsheet 38 and the breathable microporous film 40B that extend beyond the edges of the absorbent core are preferably also joined to each other. The topsheet 38 and the breathable microporous film 40B can be joined in any suitable manner known in the art for this purpose. Preferably, in the embodiment shown, these portions of the topsheet 38 and the breathable microporous film 40B are joined using adhesives over substantially the entire portions that extend beyond the edges of the absorbent core 42, and a crimp seal at the end edges 28 of the main body portion where the topsheet 38 and backsheet 40 are densified by the application of pressure or heat and pressure.

The sanitary napkin 20 shown in FIGS. 1 and 2 also comprises a pair of flaps 24 that are joined to the main body portion 22 along a juncture, such as lines of juncture 52. The flaps 24 extend laterally outward beyond the longitudinal side edges 26 of the main body portion 22 from their proximal edges to their distal edges (or "free end"). The flaps 24 comprise a flap topsheet 44 and a flap backsheet 46. In the embodiment shown in FIGS. 1 and 2, the flaps 24 are integral with the main body portion 22, that is, the flap topsheet 44 and the flap backsheet 46 comprise integral extensions of the topsheet 38 and the breathable microporous film 40B, respectively. In the preferred embodiment, the apertured formed film 40A does not extend into the flaps 24.

The extensions of the topsheet 38 and the breathable microporous film 40B of the flaps 24 (i.e., the flap topsheet 44 and the flap backsheet 46) may be joined by any suitable method, such as adhesive attachment, ultrasonic attachment, heat attachment or the like. In the preferred embodiment, the extensions of the topsheet 38 and the breathable microporous film 40B are joined by applying adhesive to substantially all the region of the flaps 24.

The topsheet 38 is preferably compliant, of feeling, and non-irritating to the wearer's skin. Further, the topsheet 38 is fluid pervious, permitting fluid to readily penetrate through its thickness. A suitable topsheet 38 may be manufactured from a wide range of materials such as woven and nonwoven materials; polymeric materials such as apertured formed thermoplastic films, apertured plastic films, and hydroformed thermoplastic films; porous foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); or from a combination of natural and synthetic fibers. A preferred topsheet comprises an apertured formed film. In the embodiment, apertured formed films are preferably used for the topsheet because they are pervious to body exudates and yet non-absorbent and have a reduced tendency to allow fluids to pass; back through and rewet the wearer's skin. Thus, the surface of the formed film which is in contact with the body remains dry, thereby reducing body soiling and creating a more comfortable feel for the wearer. Suitable apertured formed films are described in U.S. Pat. No. 3,929,135 issued to Thompson, on Dec. 30, 1975; U.S. Pat. No. 4,324,246 issued to Mullane et al., on Apr. 13, 1982; U.S. Pat. No. 4,342,314 issued to Radel, et al., on Aug. 3, 1982; U.S. Pat. No. 4,463,045, issued to Ahr, et al., on Jul. 31, 1984 and U.S. Pat. No. 5,006,394 issued to Baird, on Apr. 9, 1991.

The backsheet 40 is preferably impervious to liquid and pervious to vapor. The primary role of the backsheet 40 is to prevent the extrudes absorbed and contained in the absorbent core 42 from wetting articles that contact the absorbent product such as, underpants, pants, pajamas and undergarments. In addition however, the backsheet 40 also permits the transfer of both vapor and air through it and thus allows the circulation of air into and out of the backsheet 40.

In the embodiment shown in FIG. 2, the backsheet 40 comprises two layers; a first layer comprising a gas permeable apertured formed film layer 40A and a second layer comprising a breathable microporous film layer 40B. The first layer 40A is typically located adjacent to the absorbent core 42 and subsequent layers of the backsheet are typically located further away from the absorbent core 42. The backsheet 40 may comprise additional layers. All of the layers of the backsheet 40 can be substantially in intimate and direct contact with one another.

Figure 3:
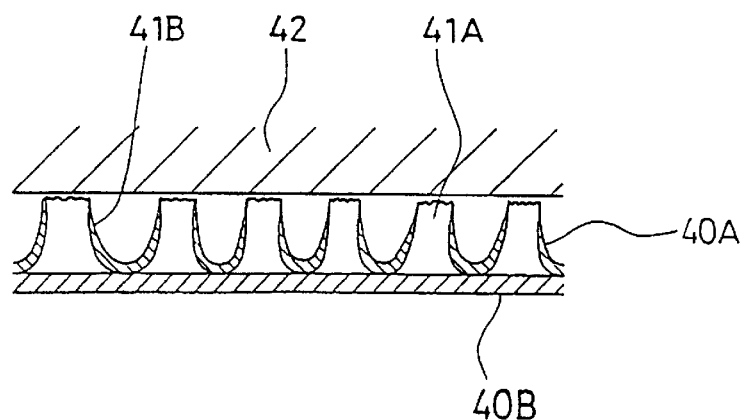
FIG. 3 is a fragmentary enlarged cross-sectional view of a part of the absorbent core and a part of the backsheet of the sanitary napkin.

As shown in FIG. 3 which shows an enlarged cross sectional view of the backsheet 40 with a part of the absorbent core 42, the first layer of the apertured formed film 40A comprises a layer having discrete apertures 41A which extend beyond the horizontal plane of the garment facing surface of the layer towards the absorbent core 42 thereby forming protuberances 41B. Each protuberance 41B has an orifice located at its terminating end. Preferably the protuberances 41B have a funnel or conical shape, similar to those described in U.S. Pat. No. 3,929,135. The apertures located within the plane of the layer and the orifices located at the terminating end of protuberances themselves maybe circular or non circular. In any case the cross sectional dimension or area of the orifice at the termination of the protuberance is smaller than the cross sectional dimension or area of the aperture located within the plane of the layer. The first layer 40A of the backsheet 40 may be made of any material known in the art, but is preferably manufactured from commonly available polymeric materials. The first layer 40A may also comprise any type of formed films which may be used for a topsheet as described above.

The second layer 40B of the backsheet 40 may comprise a breathable microporous film composed of a thermoplastic resin and inorganic fillers dispersed in the thermoplastic resin. Suitable thermoplastic polymers include polyolefins such as polyethylenes, including liner low density polyethylene (LLDPE), low density polyethylene (LDPE), ultra low density polyethylene (ULDPE), high density polyethylene (HDPE), or polypropylene and blends thereof with the above and other materials. Examples of other suitable thermoplastic polymers which may also be used include, but are not limited to, polyester, polyurethanes, compostable or biodegradable polymers, thermoplastic elastomers, and metallocene catalyst-based polymers (e.g., INSITE® available from Dow Chemical Company and Exxact® available from Exxon). The inorganic material or filler is selected from the group consisting of calcium carbonate, clay and titanium dioxide, with the preferred inorganic filler being calcium carbonate. The inorganic filler may be coated with a fatty acid ester to obtain higher loadings in the polymer. The inorganic filler and the thermoplastic polymer are blended together to form a homogeneous mixture in a suitable mixing extruder, or in a separate preliminary compounding step. The mixture is then cast or blown into a film. The obtained film is stretched at least in one direction to impart breathability on the substantially entire area of the film. The step of stretching a film to impart breathability may be done at a different place prior to manufacturing process of absorbent articles. Alternatively, the step of stretching may be done at the same place, i.e., same manufacturing process, prior to assembling a breathable microporous film with other elements of absorbent articles. In any case, the film is imparted breathability on the substantially entire area of the film before the resulting breathable microporous film is assembled with other elements of absorbent articles.

The first layer 40A and the second layer 40B have breathability. The water vapor transmission rate (WVTR) of the backsheet 40 comprising the first layer 40A and the second layer 40B is important in reducing the incidence of skin problems associated with high humidity conditions. The backsheet 40 has a water vapor transmission rate of at least about 200 g/m²/24 hr, preferably at least about 430 g/m²/24 hr, more preferably at least about 580 g/m²/24 hr. The first layer 40A has much higher water vapor transmission rate than the second layer 40B because the first layer 40A is an apertured formed film as opposed to the fact that the second layer 40B is a breathable microporous film. The water vapor transmission rate of the second layer 40B which is a breathable microporous film is important because the water vapor transmission rate of the backsheet 40 is limited by the water vapor transmission rate of the second layer 40B being lower than that of the first layer 40A. The second layer 40B has a water vapor transmission rate of at least about 250 g/m²/24 hr, preferably at least about 480 g/m²/24hr, more preferably at least about 630 g/m²/24 hr. The water vapor transmission rate of the first layer 40A may have at least ten times as high as that of the second layer 40B.

The water vapor transmission rate (WVTR) is measured by the outlined method set forth below. This test method is a validated standard ASTM method (E96-80) detailed on page 746 of Annual book of ASTM standards 1996. A sample is climatised (23° C. and 50% RH) 1 hour before the starting of the test. A sample material is placed on the top of the cup and held securely by a retaining ring and gasket. A known amount of water is put into a cup. The level of the water at the start of the test is 19 mm from the sample lower surface. The assembly is then weighed and recorded as the initial weight. The assembly is placed in a constant temperature (23° C.) and humidity (50% RH) chamber for 24 hours. The sample is placed in front of a fan that is able to generate an air stream over the top of the sample cup of 3 m/sec. Following the set test duration, the assembly is then removed from the chamber. The assembly is then weighed and recorded as the final weight. The water vapor transmission rate (WVTR) is calculated and expressed in g/m²/24 hr using the following formula $$WVTR = \frac{\text{Initial weight} - \text{Final weight}}{\text{Area of sample in meters}}$$

The absorbent core 42 may be any absorbent means which is generally compressible, conformable, resilient, non-irritating to the wearer's skin and capable of absorbing and containing body exudates. The absorbent core 42 may be manufactured from a wide variety of fluid absorbent materials commonly used in disposable sanitary napkins, and other disposable absorbent articles. Examples of suitable absorbent materials include comminuted wood pulp (which is generally referred to as airfelt), creped cellulose wadding, modified cross-linked cellulose fibers (such as those described in U.S. Pat. No. 5,217,445 issued to Young, et al., on Jun. 8, 1993), capillary channel fibers (that is, fibers having intra-fiber capillary channels such as those described in U.S. Pat. No. 5,200,248 issued to Thompson, et al., on Apr. 6, 1993), absorbent foams (such as those described in U.S. Pat. No. 5,260,345 issued to DesMarais, et al., on Nov. 9, 1993 and U.S. Pat. No. 5,268,244 issued to DesMarais, et al., on Dec. 7, 1993), thermally bonded airlay materials (such as those material described in U.S. Pat. No. 5,607,414 issued to Richards, et al., on Mar. 4, 1997), hydrogel-forming polymer gelling agents (such as those material described in U.S. Pat. No. 4,673,402 issued to Weisman, et al., on Jun. 16, 1987 and U.S. Pat. No. 4,935,022 issued to Lash et al., on Jun. 19, 1990), absorbent sponges, synthetic staple fibers, polymeric fibers, peat moss, or any equivalent materials or combinations of materials. Further, the absorbent core 42 may comprise a first portion and a second portion, the first portion comprising the following components: (a) an optional primary fluid distribution layer preferably together with a secondary optional fluid distribution layer; (b) a fluid storage layer; and the second portion comprising (c) an optional fibrous layer underlying the storage layer; and (d) other optional components. Such a structure is disclosed in PCT publication WO 97/24096 published on Jul. 10, 1997 and WO 97/24095 published on Jul. 10, 1997.

The sanitary napkin 20 shown in FIG. 1 preferably has a zone of deformation. Herein "zone of deformation" refers to a region or portion in which a material is permanently mechanically deformed. In the embodiment, the zone of deformation includes a zone of extensibility 56 and a deformed region that forms a hinge 54.

The hinge 54 has a generally longitudinally-oriented, mechanically-deformed region. The hinge 54 provides a region of the sanitary napkin 20 with increased flexibility to create preferred bending axes for the flaps 24 to bend or fold about. The hinge 54 is preferably located in a region along the juncture 52 of the flaps 24 with the main body portion 22. The hinge 54, however, does not have to coincide exactly with the juncture 52 of the flaps 24 with the main body portion 22. The hinge 54 can be located laterally inboard of the juncture 52 of the flaps with the main body portion 22, on the juncture, laterally outboard of the juncture, or any combination of the foregoing. If the hinge 54 is located laterally inboard of the juncture or on the juncture, the hinge 54 may be considered to be formed in at least part of the main body portion 22 (and, in the latter case, also in part of the flaps 24).

The hinge 54 can extend along the entire juncture 52 of the flaps with the main body portion, or along only a portion thereof. If the hinge 54 is only provided along a portion of the juncture 52, it is preferably provided in the region of the sanitary napkin 20 surrounding and including the flap transverse centerline. The hinge 54 can be in many possible configurations. The hinge 54 can comprise a continuous region, or a plurality of spaced apart intermittent regions. The hinge 54 can be rectilinear, curvilinear, or it can comprise portions that are rectilinear and portions that are curvilinear. The hinge 54 has a laterally inwardmost, or proximal, boundary and an outermost, or distal, boundary.

The hinge 54 can be formed in any suitable manner that provides the desired region of the sanitary napkin with increased flexibility. Preferably, the hinge 54 is formed by mechanically deforming the desired regions of the sanitary napkin. It has been found that many processes suitable for providing regions of the sanitary napkin with extensibility are particularly suitable for providing regions of the sanitary napkin 20 selected for the hinge 54 with enhanced flexibility.

The hinge 54 can, for instance, be formed by a process which has been described as pre-corrugating (or "ring rolling"). Suitable methods for ring rolling are described in U.S. Pat. No. 4,107,364 issued to Sisson on Aug. 15, 1978, U.S. Pat. No. 4,834,741 issued to Sabee on May 30, 1989, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992.

Alternatively, as shown in FIG. 1 for purposes of illustration, the hinge 54 is provided by forming a strainable network in the region along the juncture 52 of the flaps 24 with the main body portion 22. The process for forming a strainable network region, and structures formed thereby are described in allowed U.S. patent application Ser. No. 08/203,087 filed in the name of Chappell, et al. on Feb. 28, 1994 (PCT Publication No. WO 95/03765, published Feb. 9, 1995).

The zones of extensibility 56 relieve the stresses that develop in the flaps when they are folded down and under a wearer's undergarment. Herein "zone of extensibility" refers to a portion of the sanitary napkin 20 which is capable of extending (and is preferably capable of extending a greater amount than surrounding portions of the sanitary napkin 20). The sanitary napkin 20 preferably has at least one zone of extensibility 56 for each flap 24, and more preferably has four zones of extensibility 56, one in each quarter of the sanitary napkin 20. Since the zones of extensibility 50 relieve stresses in the flaps, they may be referred to herein as a type of "stress relief means".

The zones of extensibility 56 can be extensible in any desired direction, or in more than one direction. However, the zones of extensibility 56 are preferably primarily extensible generally outward in the transverse direction. Herein "generally in the transverse direction" means that the extensibility has a transverse component. All of the extension, however, need not be exactly parallel to the principal transverse centerline of the sanitary napkin. The extensibility, however, is preferably oriented more in the transverse direction than in the longitudinal direction.

The zones of extensibility 56 can comprise any structure capable of extending in the transverse direction (or in any other direction desired). The extensibility referred to herein, however, should be elasticless. That is, it should be accomplished without the use of separate elastic pieces, strands, or materials to contract one or more portions of the sanitary napkin. The zones of extensibility must also be accomplished without slitting or notching portions of the sanitary napkin that cover the wearer's undergarments. The zones of extensibility 56, therefore, comprise continuous material. This will have the advantage that exudates will not be able to travel through the slits or notches to soil the wearer's undergarments.

Suitable structures for the zones of extensibility 56 include, but are not limited to zones of material that are mechanically strained, corrugated, "ring rolled", formed with a strainable network therein, formed with a network of corrugations without any less extensible bands therein, folded, pleated, or joined along a curved juncture. These structures (although shown only as being part of the flaps 24), can comprise portions of the main body portion 22, portions of the flaps 24, or both. They can be integral parts of these components of the sanitary napkin, or separate elements, such as pieces of material, joined to the sanitary napkin. Suitable structures for the zones of extensibility are described in greater detail in U.S. Pat. No. 5,389,094 issued to Lavash, et al. on Feb. 14, 1995.

Examples of a zone of extensibility and a hinge are disclosed in PCT publication WO 97/12576 published on Apr. 10, 1997.

A base material having a zone of deformation (e.g., a zone of extensibility and/or higne) may be a single layer of material or laminate of materials, such as a film laminate. Preferably, in the embodiment, the base material (composite sheet) that has extensibility therein comprises a laminate formed by an extension of the topsheet 38 and the breathable microporous film 40B.

Figure 4:
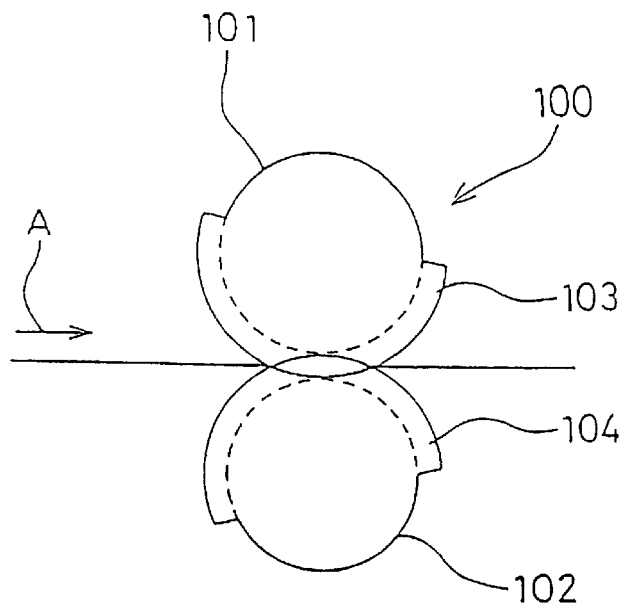
FIG. 4 is a side elevational view of the ring rolling unit used for making the sanitary napkin.
Figure 5:
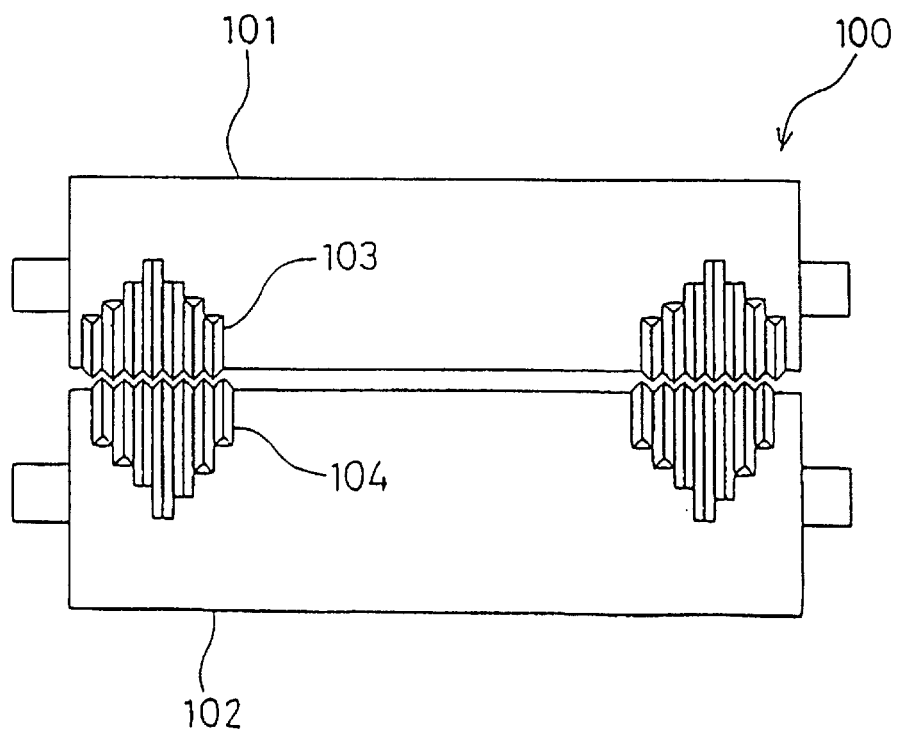
FIG. 5 is a front elevational view of the ring rolling unit used for making the sanitary napkin.
Figure 6:
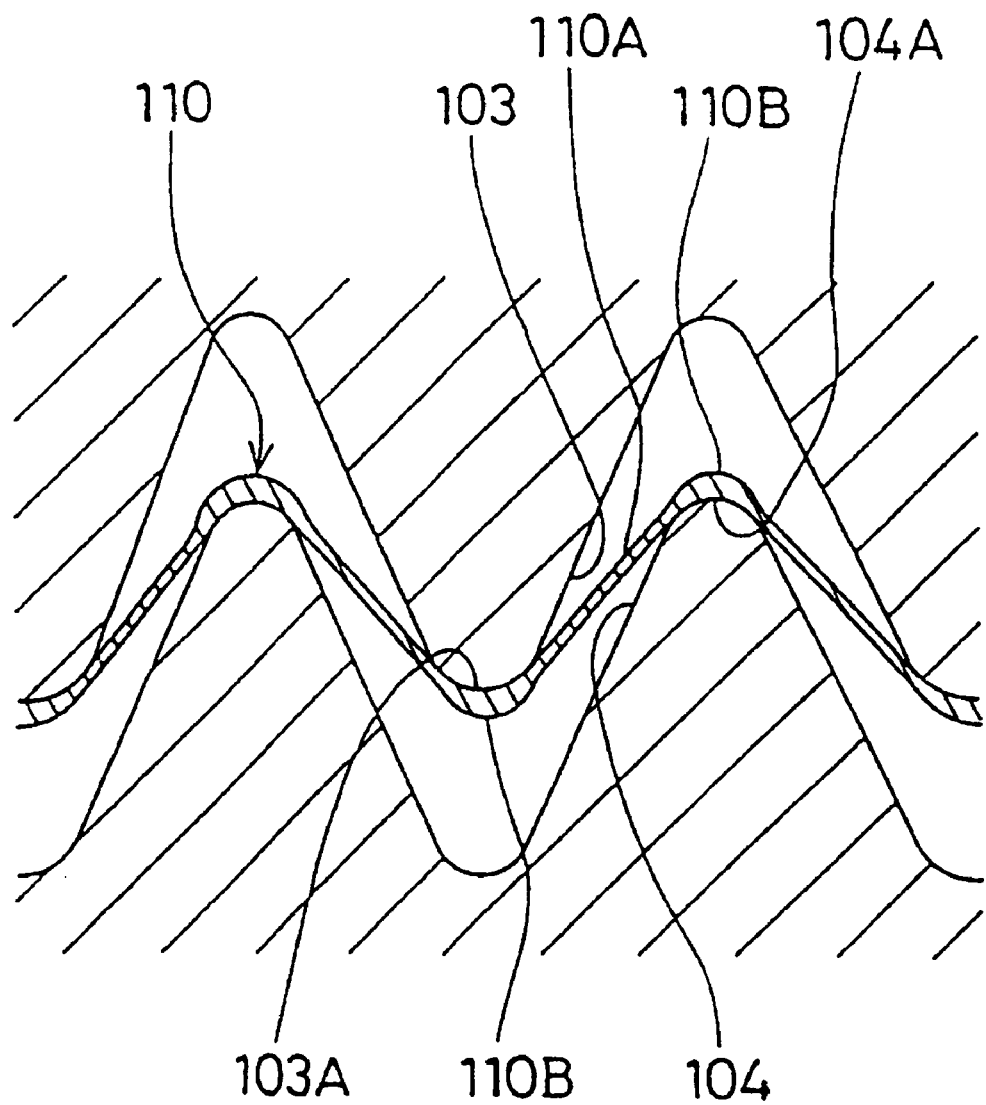
FIG. 6 is a fragmentary enlarged cross sectional view of the tooth engagement of the ring rolling unit shown in FIG. 5.

Referring to FIGS. 4 and 5, there is shown a ring rolling unit 100 used to form the zone of extensibility 56 as well as the hinge 54. The ring rolling unit 100 includes intermeshing rolls 101 and 102. The rolls 101, 102 include a plurality of intermeshing teeth 103, 104 respectively on the surfaces of the rolls along the circumferential direction of the rolls 101, 102. In one embodiment, the teeth in this embodiment preferably have a height of 3.175 mm, and are evenly spaced with the centerlines of the teeth spaced apart at 1.9 mm pitches. The entire shape of each toothed regions of the rolls 101 and 102 is generally the same as the entire shape of the zone of extensibility 56 and the hinge 54 of the sanitary napkin 20 shown in FIG. 1. The rolls 101, 102 are arranged so that the teeth 103 and 104 engage to each other as shown in FIG. 6. The engagement of the teeth 103 and 104 is determined based on desired extensibility. For example, the tooth engagement of 2.11 mm, 2.26 mm and 2.31 mm is preferably used to obtain extensibility of 75%, 80% and 85%, respectively.

The base material 110 positioned between the rolls 101 and 102 is deformed by application of an "applied strain". The term "applied strain" refers to a strain applied to a material to obtain a residual strain by deformation. The applied strain is described by a strain distribution which is characterized by the average applied strain and the standard deviation of the applied strain. When the base material 110 is subjected to the applied strain, a portion 110A of the base material 110 between the ridge 103A of the tooth 103 and the ridge 104A of the tooth 104 is mechanically strained by the applied strain and incrementally and plastically deforms so that a residual strain remains on the base material 110, while portions 110B of the base material 110 on the ridge 103A and 104A are not strained or strained only a little. Since the base material 110 tends to be strained only at the portion 110A between the ridges on the teeth next to each other and the applied strain is not necessarily applied constantly (the applied strain may be sometimes bigger than a desired applied strain or may be smaller than a desired applied strain), the portion 110A of the base material 110 may be strained exceeding a material strain at break of the base material 110. When this occurs, the base material 110 ruptures. The term "material strain at break" refers to a strain at which a material breaks or ruptures. The material strain at break is also described by a strain distribution which is characterized by the average material strain at break and the standard deviation of the material strain at break.

Extensibility of the zone of extensibility 56 may be from about 50% to about 100%. Preferably, extensibility of the zone of extensibility 56 may be from about 65% to about 90%. In order to obtain a residual strain for extensibility of, e.g., 75% on the base material, the base material must be strained beyond the residual strain. In one example, the base material comprising an apertured formed film which is marketed as Code No. X-15507 by Tredegar Film Products and a polyethylene film which is marketed as Code No. DH-215 Sofflex Blue 240 by Clopay Plastic Products Company needs to be strained up to 210% to obtain residual strain for extensibility of 75% on the base material. In this example, since the polyethylene film is non-microporous film, the base material is capable of being strained up to 210% without rupturing or creating many visible pin holes. However, the base material comprising a breathable microporous film may not be capable of such high strain without rupturing or many visible pin holes created because a breathable microporous film is weaker against a strain to obtain a residual strain for extensibility than a non-microporous film and easy to rupture. This is because the breathable microporous film undergoes the "second time" strain for obtaining a residual strain (the "first time strain is applied when stretching a film for imparting breathability). Thus, a breathable microporous film has lower material strain at break than a non-microporous film. In order to obtain extensibility of about 50% to about 100% in the zone of extensibility 56, the base material is subjected to an average applied strain of about 170% to about 260%. In order to obtain extensibility of about 65% to about 90% in the zone of extensibility 56, the base material is subjected to an average applied strain of about 190% to about 240%.

The relationship between the applied strain to obtain a predetermined extensibility and the material strain at break of a breathable microporous film must be carefully considered to avoid rupturing or many visible pin holes created especially when a breathable microporous film is used for a base material into which extensibility is imparted.

Figure 7:
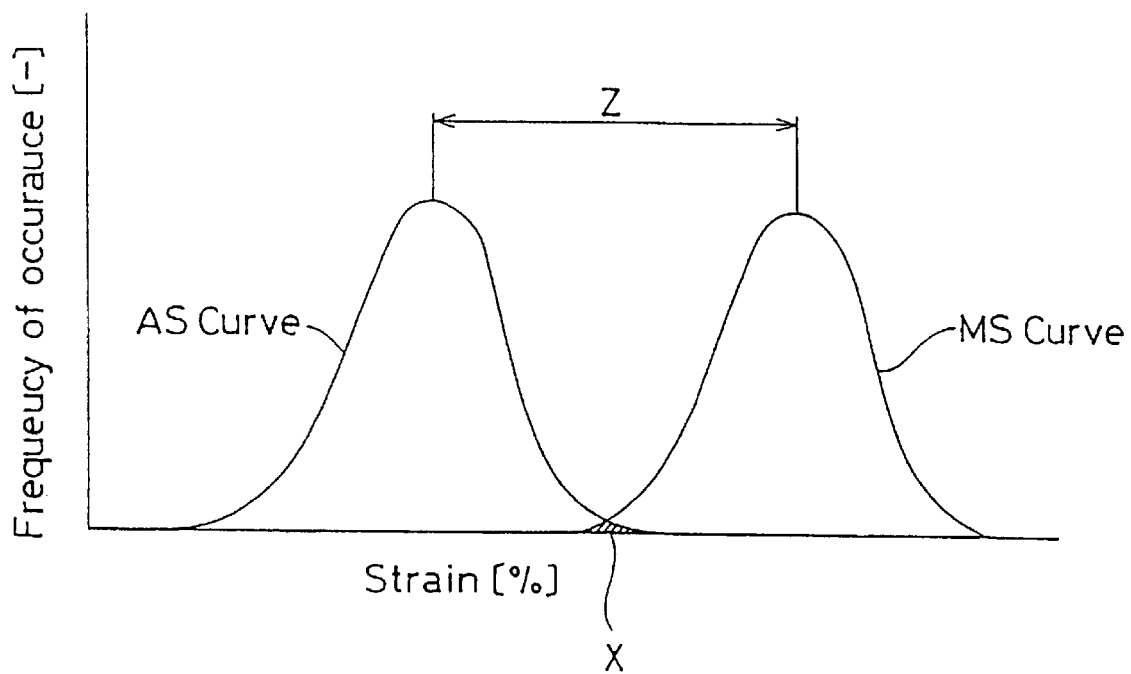
FIG. 7 is a graph showing a relationship between strain distribution for the applied strain (AS curve) to obtain a predetermined extensibility and strain distribution for the material strain at break (MS curve)

FIG. 7 shows a relationship between strain distribution for an applied strain (AS curve) to obtain a residual strain for a predetermined extensibility and strain distribution for a material strain at break (MS curve) of the breathable microporous film. The applied strain and the material strain at break can be measured by the method described below. The strain distribution of the applied strain and the material strain at break is described by a Gauss curve with standard deviations of $\sigma_{MS}$ and $\sigma_{AS}$, respectively. When both curves overlaps in the area X as shown in FIG. 7, there is a possibility that the applied strain exceeds the material strain at break of the breathable microporous film. When this occurs, the breathable microporous film ruptures or breaks (or visible pin holes created). Therefore, the less the overlapping area X, the less rupturing or the visible pin holes created occurs.

"Z" number specified by a following equation is preferably 3.0 or above when a breathable microporous film is deformed, e.g., to obtain extensibility therein. More preferably, Z number is 3.5 or above. Z number refers to a number of standard deviation between material strain at break and applied strain to obtain a residual strain for deformation, e.g., to obtain extensibility.

$$Z = \frac{N \cdot MS - AS}{\sigma_C}$$
$$= \frac{N \cdot MS - AS}{\sqrt{\sigma_{AS}^2 + \sigma_{MS}^2}}$$

wherein

MS: average material strain at break of breathable microporous film

AS: average applied strain for deformation, e.g., to obtain the predetermined extensibility N: neck down prevention coefficient, which is a coefficient to calibrate possible neck down on the material perpendicular to the direction where the "applied strain" is applied on the material $\sigma_c$: combined standard deviation of $\sigma_{MS}$ and $\sigma_{AS}$, which is described by the following equation using $\sigma_{AS}$ and $\sigma_{MS}$ $\sigma_c^2 = \sigma_{AS}^2 + \sigma_{MS}^2$ $\sigma_{MS}$: standard deviation of material strain at break $\sigma_{AS}$: standard deviation of applied strain If the base material is a composite sheet comprising a breathable microporous film and other sheets, then the above "breathable microporous film" may be read as "composite sheet".

When the material strain at break and the applied strain satisfy the above condition, rupturing of the breathable microporous film is extremely reduced and visible pin holes created are reduced to the level at which the consumers do not see products as defect.

The AS curve can be shifted away from the MS curve, so that the overlapping area of the AS curve and the MS curve is reduced, by changing such as a residual strain for extensibility. Narnely, if the lower extensibility is required, the applied strain to obtain, a residual strain for a predetermined extensibility can be lowered. On the other hand, the MS curve can be shifted away from the AS curve by changing material strain at break. Preferably, the average material strain at break of the breathable microporous film is at least about 300%, more preferably at least about 460%. Although it is preferable that the breathable microporous film has higher average material strain at break, the required minimum water vapor transmission rate of the breathable microporous film substantially limits the maximum average material strain at break of the breathable microporous film. Generally, the breathable microporous film with lower water vapor transmission rate has higher average material strain at break because of less number of micropores and/or smaller micropores in the film. However, because there is a required minimum water vapor transmission rate of the breathable microporous film as a backsheet of an absorbent article, the water vapor transmission rate can not be lowered below the required minimum water vapor transmission rate. Therefore, the average material strain at break of the breathable microporous film can not be raised so high to the extent that the breathable microporous film is capable of any level of applied strain. The maximum average material strain at break of the breathable microporous film is about 650% for the breathable microporous film to have a minimum water vapor transmission rate of about 250 g/m$^2$/24 hr. Alternatively, other physical parameters may be changed to reduce the overlapping area of the AS curve and MS curve.

The basis weight of a breathable microporous film is another factor to shift the MS curve away from the AS curve. A breathable microporous film has lower average material strain at break than a non-microporous film. This can be improved by raising the basis weight of the film since the film becomes more capable of being strained without rupturing. When the breathable microporous film has a basis weight of 30 g/m$^2$ or above, it works well to obtain a residual strain for a predetermined extensibility of from about 50% to about 100%. The breathable microporous film having a basis weight of 35 g/m$^2$ or above is more preferable. When the breathable microporous film has the above basis weight, rupturing of the breathable microporous film is extremely reduced and visible pin holes created are reduced to the level at which the consumers do not see products as defects.

Further, controlling the particle size of inorganic fillers of a breathable microporous film is a factor to avoid the breathable microporous film rupture. When the breathable microporous film includes the inorganic fillers with particle size of 20 mm or less, it works well to obtain a residual strain for a predetermined extensibility of from about 50% to about 100%. When the breathable microporous film includes the inorganic fillers with particle size of 20 mm or less, rupturing of the breathable microporous film is extremely reduced and visible pin holes created are reduced to the level at which the consumers do not see products as defects.

At least the breathable microporous film may be heated before the breathable microporous film is subjected to an applied strain. Heating the breathable microporous film helps temporarily raising the average material strain at break of the breathable microporous film without reducing the water vapor transmission rate, and temporarily shifts the MS curve away from the AS curve. Therefore, heating the breathable microporous film is especially useful when the maximum average material strain at break of the breathable microporous film is limited by the water vapor transmission rate of the film and the breathable microporous film is subjected to relatively higher strain to obtain higher extensibility on the breathable microporous film. The breathable microporous film may be heated such that the breathable microporous film is in a temperature of at least 40° C., preferably at least 43° C., more preferably at least 45° C., when the breathable microporous film having an average material strain at break of not greater than about 650% and the water vapor transmission rate of at least about 250 g/m$^2$/24 hr is subjected to an average applied strain of about 170% to about 260% to obtain extensibility of about 50% to about 100%. As the temperature of the breathable microporous film becomes higher, the breathable microporous film becomes softer and becomes capable of being stretched more without rupture of the breathable microporous film. However, the breathable microporous film should not be heated beyond the melting point of the breathable microporous film. If the breathable microporous film constitutes the base material together with other materials such as a flap topsheet, the base material should not be heated beyond the melting point of the material having the minimum melting point. In an embodiment, the base material made of an apertured formed film (flap topsheet) comprising polyethylene and a breathable microporous film comprising polyethylene and calcium carbonate should not be heated beyond a temperature of 123° C.

Figure 8:
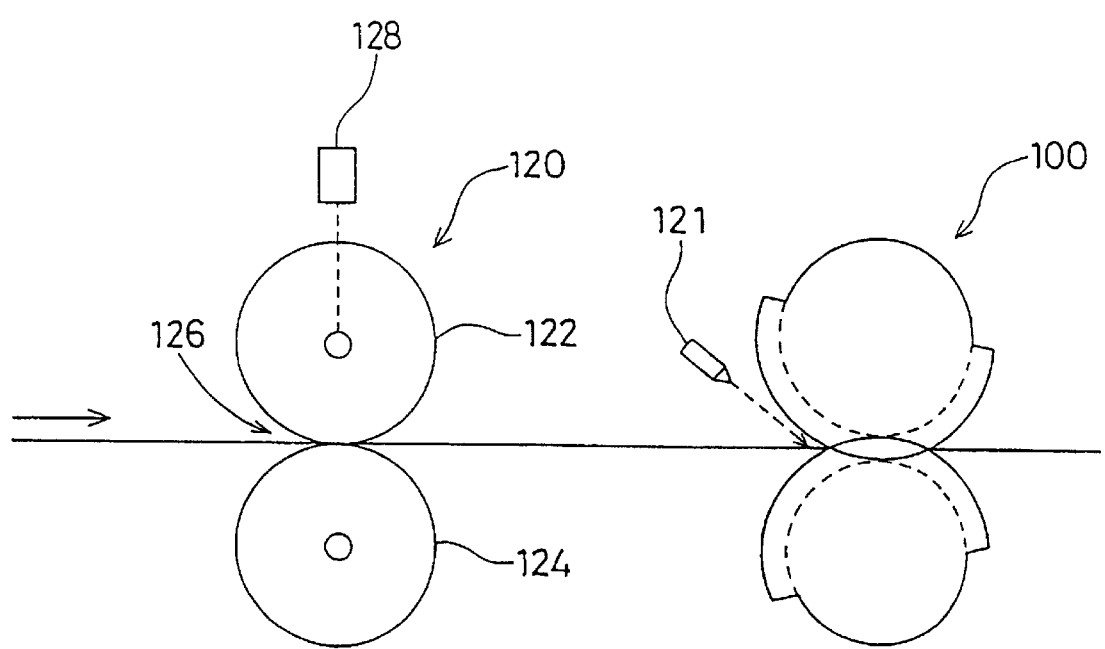
FIG. 8 is a side elevational view of the heating unit and the ring rolling unit for making the sanitary napkin.

FIG. 8 shows one preferred embodiment of heating unit 120 of the base material. The heating unit 120 includes an upper roll 122 and a lower roll 124. The base material which constitutes a part of the sanitary napkin 20 is forwarded into the nip 126 of the heating unit 120. The upper roll 122 is connected with an ultrasonic vibration system 128 to heat the base material. The heating unit 120 should heat at least the portion of the base material being subjected to straining process. Alternatively, the heating unit 120 may heat the whole of the base material. However, it is preferable that the heating unit 120 heats only a portion of the base material required being heated to save energy supplied to the heating unit 120 and to avoid giving unnecessary thermal history to the base material. In FIG. 8, the lower roll 124 may also be connected with an ultrasonic system. The heating unit 120 may be disposed as close as the ring rolling unit 100 so that the temperature of the base material does not lower during the base material traveling fromn the heating unit 120 to the ring rolling unit 100. While the heating unit 120 using an ultrasonic vibration system 128 heightens temperature of the base material, the temperature of the heating unit 120 itself does not rise so high. Therefore, using the ultrasonic vibration system 128 allows the heating unit 120 to be placed closer to the ring, rolling unit 100 without thermal influence to the ring rolling unit 100. However, it is still necessary to give a little higher temperature at the heating unit 100 to the base material to maintain the required temperature at the position of the ring rolling unit 110. The base material temperature when being subjected to straining process at the ring rolling unit 110 is important to avoid the base material rupturing. The base material temperature at the ring rolling unit 100 may be represented by the temperature of the base material at the entrance of the ring rolling unit 100. In one example, when the distance between the nip of the heating unit 120 and the entrance of the ring rolling unit 110 is about 0.5 meters. and the base material travels at the speed of about 2.8 meters/second, the base material temperature of about 57° C. to 58° C. at the nip 126 of the heating unit 120 is required to maintain the base material temperature of about 50° C. at the entrance of the ring rolling unit 110. As shown in FIG. 8, a non-contact temperature detector 121 measures the temperature of the base material at the entrance of the ring rolling unit. An example of such a non-contact temperature detector is obtainable from Minolta Camera as #TA0510F. The temperature detector 121 should measure the temperature of the portion of the base material heated by the heating unit 120 and being subjected to straining process. Further, the temperature detector 121 should be disposed to measure the temperature of the heated side of the base material if only one side of the base material is heated. As explained, in the preferred embodiment, the base material comprises as laminate formed by an extension of the topsheet 38 and the breathable microporous film 40B. The heating unit 120 heats at least the side of breathable microporous film 40B and the temperature detector 121 measures the temperature of the side of the breathable microporous film 40B.

Figure 9:
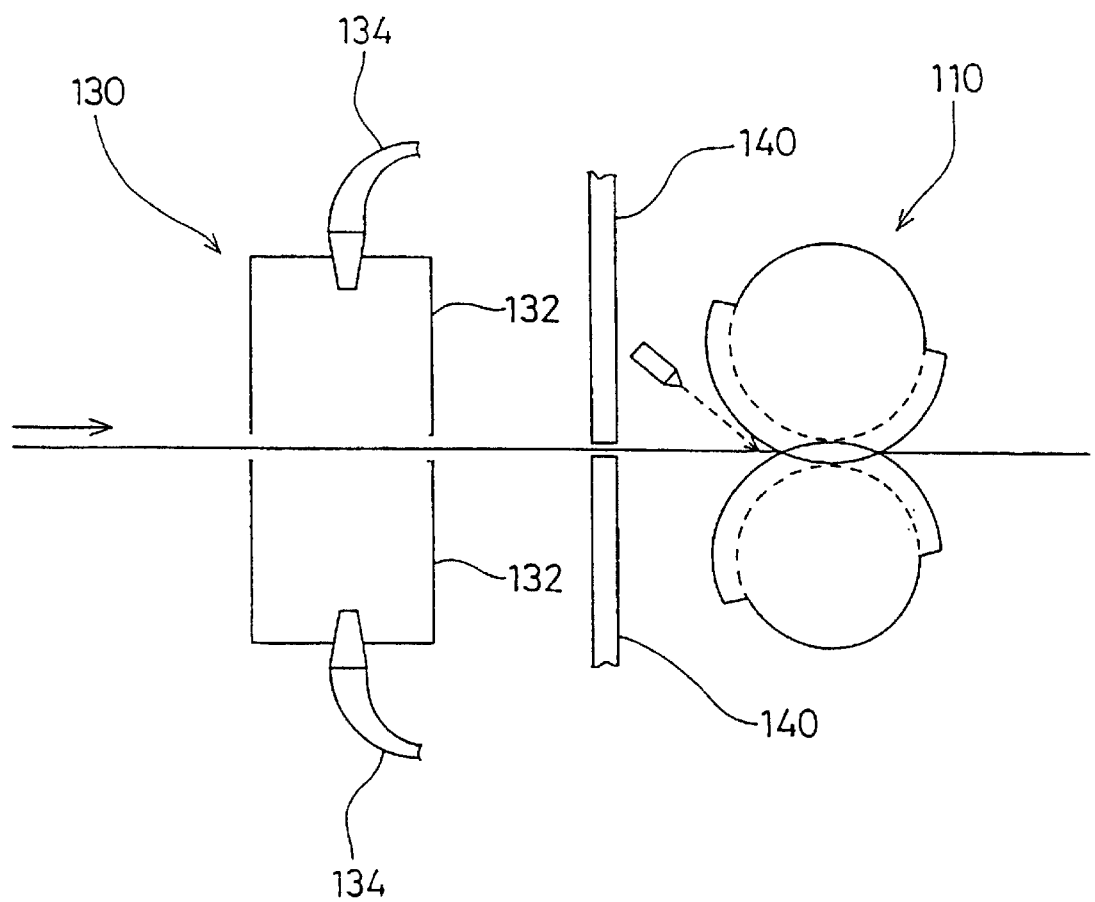
FIG. 9 is a side elevational view of an alternative embodiment of the heating unit and the ring rolling unit.

FIG. 9 shows alternative embodiment of the heating unit of the base material. The heating unit 130 includes upper and lower heating boxes 132 and upper and lower hot air blowers 134. The hot air blower 134 provides hot air into the space encompassed by the heating box 132, thereby heating the base material. The heating box 132 and the hot air blower 134 may be provided only at either of upper side or lower side with respect to the path of the base material. The heating box 132 should have a low thermal conductivity so that the heating box 132 does not transfer heat to the atmosphere. An isolation plate 140 may be provided between the heating unit 130 and the ring rolling unit 110 not to transfer heat of the heating box 132 to the ring rolling unit 110. Providing the isolation plate 140 allows the heating unit 130 to be placed closer to the ring rolling unit 100. Alternatively, the heating unit may utilize other systems, such as an infra-red radiant heater or a heating roll.

Measurement Method for Applied Strain

The samples used for this measurement are polyethylene film which have a grid pattern on the surface of the film and a grid pattern is drawn parallel to and perpendicular to the direction of extensibility which is applied by a ring rolling process. Grid interval length is preferably 1/20 or less of intermeshing teeth pitch. Samples have suitable width to cover the entire shape of each intermeshing teeth 103 and 104. Preferably, the sample is the same as breathable microporous film (evaluated film). In the case where the sample material for this test is different from evaluated film, selected sample material properties are similar to the evaluated material.

The sample is stretched throughout the ring rolling unit 100 at each required strain rate and each required strain to obtain a residual strain for a predetermined extensibility on the sample. The sample stretched indicates visible strain distribution with a grid pattern transformation. Visible strain distribution on the sample surface is photographed. Each grid length on the photography parallel to the direction of extensibility which is applied by the ring rolling unit 100 is measured by a steel ruler. Measurement of each grid length is conducted in stretched area. Each grid strain is calculated by the length change from the original grid interval length. Applied strain by the process can be obtained from each grid strain.

Measurement Method for Material Strain

The tensile test is used for measurement of material strain by measuring force versus percent elongation properties and percent available stretch of material. The tests are performed on an Instron Model 4301, available from Instron Corporation, which is interfaced to a IBM 330 computer. All essential parameters needed for measuring are input in the MTS software (Testworks 3.07) for each test. Also, all data collection, data analysis and gathering are done using the MTS software.

The sample used for this test are 1 inch wide and 4 inches long with the long axis of the sample cut parallel to the direction of extensibility of the sample which is applied by a process. The sample is cut with a sharp knife or some suitably sharp cutting device design to cut a precise 1 inch wide sample. The sample is cut so that an area representative of the symmetry of the overall pattern of the deformed region is represented. There will be cases (due to variations in either the size of the deformed portion) in which it will be necessary to cut either larger or smaller samples than is suggested herein. In this case, it is very important to note (along with any data reported) the size of the sample, which area of the deformed region it was taken from and preferably include a schematic of the representative area used for the sample. Ten samples of a given material are tested.

The grips of the Instron consist of air actuated grips designed to concentrate the entire gripping force along a single line perpendicular to the direction of testing stress having one flat surface and an opposing face from which protrudes a half round to minimize slippage of the sample. The distance (i.e., gage length) between the lines of gripping force should be 2 inches as measured by a steel ruler held beside the grips. The sample is mounted in the grips with its long axis perpendicular to the direction of applied percent elongation. The crosshead speed is set to 20 inch/min. The crosshead elongates the sample until the sample breaks at which point the crosshead stops and returns to its original position (0% elongation).

The percent available stretch is the point at which there is an inflection in the force—elongation curve, beyond which point there is rapid increase in the amount of force required to elongate the sample firther. The average of the percent available stretch for ten samples are recorded.

Calculation for Neck Down Drevention Coefficient

The tensile test is used for a preparation for calculation of neck down prevention coefficient by measuring force versus percent elongation properties and percent available stretch of material. The tests are performed on an Instron Model 4301, available from Instron Corporation, which is interfaced to a IBM 330 computer. Essential parameters needed for measuring are inpuit in the MTS software(Testworks 3.07) for each test.

The sample used for this test are 1 inch wide and 4 inches long with the long axis of the sample cut parallel to the direction of extensibility of the sample which is applied by a process. The sample is cut with a sharp exact knife or some suitably sharp cutting device design to cut a precise 1 inch wide sample. The sample is cut so that an area representative of the symmetry of the overall pattern of the deformed region is represented. There will be cases (due to variations in either the size of the deformed portion) in which it will be necessary to cut either larger or smaller samples than is suggested herein. In this case, it is very important to note (along with any data reported) the size of the sample, which area of the deformed region it was taken from and preferably include a schematic of representative area used for the sample. Ten samples of a given material are tested.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2 inches as measured by a steel ruler held beside the grips. This distance will be referred to from hereon as the "gauge length". The sample is mounted in the grips with its long axis perpendicular to the direction of applied percent elongation. The crosshead speed is set to 20 inch/min. The crosshead elongates the sample until required percent elongation at which point the crosshead stops, and returns to its original position (0% elongation ) with manual operation.

Neck down is defined as the absolute change in width of a sample due to stretching. Material is necked down at applied percent elongation. Applied percent elongation is set in MTS software and MTS software calculates movement distance to achieve required percent elongation with percent available stretch. The percent available stretch is the point at which there is an inflection in the force—elongation curve, beyond which point there is rapid increase in the amount of force required to elongate the sample further.

In the case where the sample is stretched perpendicular to the direction of applied percent elongation to prevent (recover) neck down, material breaks at lower strain (material strain at break recovered neck down) than material strain that is measured by the above method for material strain. In order to measure material strain at break recovered neck down, the material is stretched in the direction perpendicular to applied percent elongation to recover neck down at applied percent strain. Recovering neck down is done by paper clip so that the paper clip stretch the narrowest point in the width direction of the sample. When the sample breaks upon stretching for recovery, applied percent elongation is recorded as material strain at break recovered neck down. The measurement for material strain at break recovered neck down is preferably done under the same conditions (such as temperature) as the actual process for obtaining extensibility on the absorbent article.

Neck down prevention coefficient is calculated by the following formula, $$\text{Neck down prevention coefficient } (N) = \frac{\text{material strain at break recovered neck down}}{\text{average material strain}}$$

EXAMPLES

The following examples flrther describe and demonstrate the preferred embodiments within the scope of the present invention. The examples are given solely for the purpose of illustration, and are not to be construed as limitations of the present invention since many thereof are possible without departing from its spirit and scope.

(Example A-1)

A topsheet is an apertured formed film as Code No. X-15507 obtainable from Tredegar Film Products. An absorbent core is the absorbent core used in "Whisper Ultra Slim" manufactured by Procter & Gamble. A backsheet is a breathable microporous film as Code No. PG-0I obtainable from Mitsui Chemical. The breathable microporous film has average material strain at break of 563.9% with standard deviation 25.3. Neck down prevention coefficient is 0.6749. Flaps of the sanitary napkins are made of the extensions of the apertured formed film and the breathable microporous film. The apertured formed film and the breathable microporous film constituting the flaps are joined by an adhesive (Nitta Findley Co., Ltd.; code No. H-4031). The sample is processed by the process described in FIGS. 4–6 under the condition of average applied strain of 210% with standard deviation of 48.3 to obtain 75% extensibility on the flaps. In this example, Z number is 3.1.

(Example A-2)

The breathable microporous film has average material strain at break of 579% with standard deviation 17.3. Neck down prevention coefficient is 0.6646. The sample is processed under the condition of average applied strain of 219% with standard deviation of 50.4 to obtain 80% extensibility on the flaps. In this example, Z number is 3.3. The other structures are the same as the Example A-1.

(Example A-3)

The breathable microporous film has average material strain at break of 580% with standard deviation 18.2. Neck down prevention coefficient is 0.6516. The sample is processed under the condition of average applied strain of 232% with standard deviation of 53.4 to obtain 85% extensibility on the flaps. In this example, Z number is 3.0. The other structures are the same as the Example A-1.

(Example A-5)

The breathable microporous film has average material strain at break of 584% with standard deviation 16.5. Neck down prevention coefficient is 0.6749. The sample is processed under the condition of average applied strain of 210% with standard deviation of 48.3 to obtain 75% extensibility on the flaps. In this example, Z number is 3.6. The other structures are the same as the Example A-1.

(Example A-6)

The breathable microporous film has average material strain at break of 577.4% with standard deviation 14.8. Neck down prevention coefficient is 0.6516. The sample is processed under the condition of average applied strain of 232% with standard deviation of 53.4 to obtain 85% extensibility on the flaps. In this example, Z number is 3.0. The other structures are the same as the Example A-1.

(Example B-2)

The breathable microporous film has a basis weight of 35 g/m$^2$ and average material strain at break of 579% with standard deviation 17.3. The sample is processed under the condition of average applied strain of 219% with standard deviation of 50.4 to obtain 80% extensibility on the flaps. The other structures are the same as the Example B-1.

(Example B-3)

The breathable microporous film has a basis weight of 35 g/m$^2$ and average material strain at break of 580% with standard deviation 18.2. The sample is processed under the condition of average applied strain of 232% with standard deviation of 53.4 to obtain 85% extensibility on the flaps. The other structures are the same as the Example B-1.

(Example B-4)

The breathable microporous film has a basis weight of 35 g/m$^2$ and average material strain at break of 545.3% with standard deviation 27.4. The sample is processed under the condition of average applied strain of 210% with standard deviation of 48.3 to obtain 75% extensibility on the flaps. The other structures are the same as the Example B-1.

(Example B-5)

The breathable microporous film has a basis weight of 35 g/m$^2$ and average material strain at break of 548.6% with standard deviation 18.2. The sample is processed under the condition of average applied strain of 232% with standard deviation of 53.4 to obtain 85% extensibility on the flaps. The other structures are the same as the Example B-1.

(Example B-6)

The breathable microporous film has a basis weight of 40 g/m$^2$ and average material strain at break of 584% with standard deviation 16.5. The sample is processed under the condition of average applied strain of 210% with standard deviation of 48.3 to obtain 75% extensibility on the flaps. The other structures are the same as the Example B-1.

(Example B-7)

The breathable microporous film has a basis weight of 40 g/m$^2$ and average material strain at break of 577.4% with

|     | Average material strain at break (MS) [%] | $\sigma_{MS}$ | Neck down prevention coefficient (N) | Average applied strain (AS) [%] | $\sigma_{AS}$ | Obtained extensibility [%] | Z |
| --- | --- | --- | --- | --- | --- | --- | --- |
| A-1 | 563.9 | 25.3 | 0.6749 | 210 | 48.3 | 75 | 3.1 |
| A-2 | 579   | 17.3 | 0.6646 | 219 | 50.4 | 80 | 3.3 |
| A-3 | 580   | 18.2 | 0.6516 | 232 | 53.4 | 85 | 3.0 |
| A-4 | 584   | 16.5 | 0.6749 | 210 | 48.3 | 75 | 3.6 |
| A-5 | 577.4 | 14.8 | 0.6516 | 232 | 53.4 | 85 | 3.0 |
| A-6 | 627.6 | 21.9 | 0.6749 | 210 | 48.3 | 75 | 4.0 |

(Example B-1)

A topsheet is an apertured formed film as Code No. X-15507 obtainable from Tredegar Film Products. An absorbent core is the absorbent core used in "Whisper Ultra Slim" manufactured by Procter & Gamble. A backsheet is a breathable microporous film as Code No. PG-0I obtainable from Mitsui Chemical. The breathable microporous film has a basis weight of 35 g/m$^2$ and average material strain at break of 563.9% with standard deviation of 25.3. Flaps of the sanitary napkins are made of the extensions of the apertured formed film and the breathable microporous film. The apertured formed film and the breathable microporous film constituting the flaps are joined by an adhesive (Nitta Findley Co., Ltd.; code No. H-4031). The sample is processed by the process described in FIGS. 4–6 under the condition of average applied strain of 210% with standard deviation of 48.3 to obtain 75% extensibility on the flaps.

standard deviation 14.8. The sample is processed under the condition of average applied strain of 232% with standard deviation of 53.4 to obtain 85% extensibility on the flaps. The other structures are the same as the Example B-1.

(Example B-8)

The breathable microporous film has a basis weight of 40 g/m$^2$ and average material strain at break of 627.6% with standard deviation 21.9. The sample is processed under the condition of average applied strain of 210% with standard deviation of 48.3 to) obtain 75% extensibility on the flaps. The other structures are the same as the Example B-1.

(Example B-9)

The breathable microporous film has a basis weight of 40 g/m$^2$ and average material strain at break of 616.0% with standard deviation 18.0. The sample is processed under the condition of average applied strain of 210% with standard deviation of 48.3 to obtain 75% extensibility on the flaps. The other structures are the same as the Example B-1.

|  | Basic wt. of microporous film [g/m²] | Average material strain at break (MS) [%] | $\sigma_{MS}$ | Average applied strain (AS) [%] | $\sigma_{AS}$ | Obtained extensibility [%] |
|---|---|---|---|---|---|---|
| B-1 | 35 | 563.9 | 25.3 | 210 | 48.3 | 75 |
| B-2 | 35 | 579 | 17.3 | 219 | 50.4 | 80 |
| B-3 | 35 | 580 | 18.2 | 232 | 53.4 | 85 |
| B-4 | 35 | 545.3 | 27.4 | 210 | 48.3 | 75 |
| B-5 | 35 | 548.6 | 18.2 | 232 | 53.4 | 85 |
| B-6 | 40 | 584 | 16.5 | 210 | 48.3 | 75 |
| B-7 | 40 | 577.4 | 14.8 | 232 | 53.4 | 85 |
| B-8 | 40 | 627.6 | 21.9 | 210 | 48.3 | 75 |
| B-9 | 40 | 616.0 | 18.0 | 210 | 48.3 | 75 |

(Example C-1)

A topsheet is an apertured formed film as Code No. X-15507 obtainable from Tredegar Film Products. An absorbent core is the absorbent core used in "Whisper Ultra Slim" manufactured by Procter & Gamble. A backsheet is a breathable microporous film as Code No. PG-0I obtainable from Mitsui Chemical. The breathable microporous film has a basis weight of 35 g/m² and average material strain at break of 545.3% with standard deviation of 27.4. The breathable microporous film includes inorganic fillers of $CaCO_3$ with particle size of 20 mm or less. The average particle size is about 1 mm. Flaps of the sanitary napkins are made of the extensions of the apertured formed film and the breathable microporous film. The apertured formed film and the breathable microporous film constituting the flaps are joined by an adhesive (Nitta Findley Co., Ltd.; code No. H-4031). The sample is processed by the process described in FIGS. 4–6 under the condition of average applied strain of 210% with standard deviation of 48.3 to obtain 75% extensibility on the flaps.

(Example C-2)

The breathable microporous film has a basis weight of 35 g/m² and average material strain at break of 548.6% with standard deviation 18.2. The breathable microporous film includes inorganic fillers of $CaCO_3$ with particle size of 20 mm or less. The average particle size is about 1 mm. The sample is processed under the condition of average applied strain of 232% with standard deviation of 53.4 to obtain 85% extensibility on the flaps. The other structures are the same as the Example C-1.

(Example C-3)

The breathable microporous film has a basis weight of 40 g/m² and average material strain at break of 584.2% with standard deviation 16.5. The breathable microporous film includes inorganic fillers of $CaCO_3$ with particle size of 20 mm or less. The average particle size is about 1 mm. The sample is processed under the condition of average applied strain of 210% with standard deviation of 48.3 to obtain 75% extensibility on the flaps. The other structures are the same as the Example C-1.

(Example C-4)

The breathable microporous film has a basis weight of 40 g/m² and average material strain at break of 577.4% with standard deviation 14.8. The breathable microporous film includes inorganic fillers of $CaCO_3$ with particle size of 20 mm or less. The average particle size is about 1 mm. The sample is processed under the condition of average applied strain of 232% with standard deviation of 53.4 to obtain 85% extensibility on the flaps. The other structures are the same as the Example C-1.

(Example C-5)

The breathable microporous film has a basis weight of 40 g/m² and average material strain at break of 616.0% with standard deviation 18.0. The breathable microporous film includes inorganic fillers of $CaCO_3$ with particle size of 20 mm or less. The average particle size is about 1 mm. The sample is processed under the condition of average applied strain of 210% with standard deviation of 48.3 to obtain 75% extensibility on the flaps. The other structures are the same as the Example C-1.

(Example D)

The breathable microporous film has a basis weight of 35 g/m² and average material strain at break of 560.9% with standard deviation 22.8. The breathable microporous film includes inorganic fillers of $CaCO_3$ with particle size of 97% of 20 mm or less and 3% of more than 20 mm. The average particle size is about 1 mm. The sample is processed under the condition of average applied strain of 210% with standard deviation of 48.3 to obtain 75% extensibility on the flaps. The other structures are the same as the Example C-1.

|  | Particle size of fillers in microporous film [mm] | Average material strain at break (MS) [%] | Basis wt. of microporous film [g/m²] | $\sigma_{MS}$ | Average applied strain (AS) [%] | $\sigma_{AS}$ | Obtained extensibility [%] |
|---|---|---|---|---|---|---|---|
| C-1 | less than 20 | 545.3 | 35 | 27.4 | 210 | 48.3 | 75 |
| C-2 | less than 20 | 548.6 | 35 | 18.2 | 232 | 53.4 | 85 |
| C-3 | less than 20 | 584.2 | 40 | 16.5 | 210 | 48.3 | 75 |
| C-4 | less than 20 | 577.4 | 40 | 14.8 | 232 | 53.4 | 85 |
| C-5 | less than 20 | 616.0 | 40 | 18.0 | 210 | 48.3 | 75 |

-continued

|   | Particle size of fillers in microporous film [mm] | Average material strain at break (MS) [%] | Basis wt. of microporous film [g/m²] | $\sigma_{MS}$ | Average applied strain (AS) [%] | $\sigma_{AS}$ | Obtained extensibility [%] |
|---|---|---|---|---|---|---|---|
| D | 97% of 20 mm or less and 3% of more than 20 mm | 560.9 | 35 | 22.8 | 210 | 48.3 | 75 |

Examples A-1 to A-6, B-1 to B-9, and C-1 to c-5 provide a product with significantly reduced frequency of occurrence of pin holes while example D provides a product with many visible pin holes which are not acceptable for consumers.

While particular embodiments of the present invention have been illustrated and described, it would be obvious to those skilled in the art that various other changes and modifications can be made without departing from the spirit and scope of the invention.

What is claimed is:

1. An absorbent article having a breathable microporous film, the breathable microporous film made by stretching a mixture of a thermoplastic resin and inorganic fillers at least in one direction, wherein at least a part of the breathable microporous film is deformed such that Z number specified by a following equation is 3.0 or above.

$$Z = \frac{N \cdot MS - AS}{\sqrt{\sigma_{AS}^2 + \sigma_{MS}^2}}$$

wherein

MS: average material strain at break of breathable microporous film

AS: average applied strain for deformation

N: neck down prevention coefficient $\sigma_{MS}$: standard deviation of material strain at break $\sigma_{AS}$; standard deviation of applied strain.

2. The absorbent article of claim 1 wherein the Z number is 3.5 or above.

3. An absorbent article having a breathable microporous film, the breathable microporous film having extensibility, the breathable microporous film made by stretching a mixture of a thermoplastic resin and inorganic fillers at least in one direction, wherein at least a part of the breathable microporous film is imparted a predetermined extensibility by being deformed such that Z number specified by a following equation is 3.0 or above.

$$Z = \frac{N \cdot MS - AS}{\sqrt{\sigma_{AS}^2 + \sigma_{MS}^2}}$$

wherein

MS: average material strain at break of breathable microporous film

AS: average applied strain to obtain a predetermined extensibility

N: neck down prevention coefficient $\sigma_{MS}$: standard deviation of material strain at break $\sigma_{AS}$: standard deviation of applied strain.

4. The absorbent article of claim 3 wherein the Z number is 3.5 or above.

5. The absorbent article of claim 3 wherein the breathable microporous film has an average material strain at break of at least 300%.

6. The absorbent article of claim 3 wherein the average applied strain is between 170% and 260%.

7. The absorbent article of claim 3 wherein the predetermined extensibility is from 50% to 100%.

8. An absorbent article having a breathable microporous film, the breathable microporous film having extensibility, the breathable microporous film made by stretching a mixture of a thermoplastic resin and inorganic fillers at least in one direction, wherein (1) the breathable microporous film has a basis weight of 30 g/m² or above, (2) at least a part of the breathable microporous film is imparted a predetermined extensibility by being deformed, and (3) the predetermined extensibility is from 50% to 100%.

9. An absorbent article having a breathable microporous film, the breathable microporous film having extensibility. the breathable microporous film made by stretching a mixture of a thermnoplastic resin and inorganic fillers at least in one direction, wherein (1) the breathable microporous film includes the inorganic fillers with particle size of 20 mm or less, (2) at least a part of the breathable microporous film is imparted a predetermined extensibility by being deformed, and (3) the predetermined extensibility is from 50% to 100%.

10. The absorbent article of claim 9 wherein the breathable microporous film has a basis weight of 30 g/m² or above.

* * * * *

UNITED STATES PATENT AND TRADEMARK OFFICE
CERTIFICATE OF CORRECTION

PATENT NO.   : 6,328,723 B1  
DATED        : December 11, 2001  
INVENTOR(S)  : Burns, Jr. et al.

It is certified that error appears in the above-identified patent and that said Letters Patent is hereby corrected as shown below:

Title page,
Item [75], Inventors, after "Guido Bonelli" please delete "Pascara via Colle Innamorati (IT)" and insert therefor -- Pescara (IT) --.

Column 1,
Line 14, after "1990" please delete "." (the period) and insert therefor -- , -- (a comma).
Line 15, after "1993" please delete "." (the period) and insert therefor -- , -- (a comma).
Line 16, after "1996" please delete "." (the period) and insert therefor -- , -- (a comma).
Line 19, after "1995" please delete "." (the period) and insert therefor -- , -- (a comma).
Line 20, after "1996" please delete "." (the period) and insert therefor -- , -- (a comma).
Line 21, after "1996" please delete "." (the period) and insert therefor -- , -- (a comma).
Line 22, after "1996" please delete "." (the period) and insert therefor -- , -- (a comma).
Line 30, please delete "4,116.892" and insert therefor -- 4,116,892 --.
Line 31, after "1979" please delete "." (the period) and insert therefor -- , -- (a comma).
Line 32, please delete "4,289.831" and insert therefor -- 4,289,831 --.
Line 45, please delete "5,389.094" and insert therefor -- 5,389,094 --.

Column 2,
Line 23, please delete the equation and insert therefor --

$$Z = \frac{N \cdot MS - AS}{\sqrt{\sigma_{AS}^2 + \sigma_{MS}^2}}$$

--

Line 29, after "MS" please insert -- : -- (a colon).
Line 45, please delete the equation and insert therefor --

$$Z = \frac{N \cdot MS - AS}{\sqrt{\sigma_{AS}^2 + \sigma_{MS}^2}}$$

--

Column 3,
Line 24, please delete "comer" and insert therefor -- corner --.

Column 5,
Line 64, after "as" please delete "," (the comma).

UNITED STATES PATENT AND TRADEMARK OFFICE
CERTIFICATE OF CORRECTION

PATENT NO. : 6,328,723 B1
DATED : December 11, 2001
INVENTOR(S) : Burns, Jr. et al.

It is certified that error appears in the above-identified patent and that said Letters Patent is hereby corrected as shown below:

Column 11,
Line 40, please delete the equation and insert therefor --

$$Z = \frac{N \cdot MS - AS}{\sigma_c} = \frac{N \cdot MS - AS}{\sqrt{\sigma_{AS}^2 + \sigma_{MS}^2}}$$

--

Line 59, after "$\sigma_{MS}$," please insert a line break.

Column 12,
Line 7, please delete "Narnely" and insert therefor -- Namely --.
Line 8, after "obtain" please delete "," (the comma).

Column 13,
Line 48, please delete "fromn" and insert therefor -- from --.

Column 14,
Line 15, please delete "as" and insert therefor -- a --.

Column 15,
Line 38, please delete "firther" and insert therefor -- further --.
Line 40, please delete "Drevention" and insert therefor -- Prevention --.
Line 47, please delete "inpuit" and insert therefor -- input --.

Column 16,
Line 40, after "(N)" please insert a line break.
Line 48, please delete "firther" and insert therefor -- further --.

Column 17,
Line 21, please delete "A-5" and insert therefor -- A-4 --.
Line 29, please delete "A-6" and insert therefor -- A-5 --.
Line 37, (before the table), please insert (new paragraph) --
(Example A-6)
The breathable microporous film has average material strain at break of 627.6 % with standard deviation 21.9. Neck down prevention coefficient is 0.6749. The sample is processed under the condition of average applied strain of 210 % with standard deviation of 48.3 to obtain 75 % extensibility on the flaps. In this example, Z number is 4.0. The other structures are the same as the Example A-1. --.

UNITED STATES PATENT AND TRADEMARK OFFICE
CERTIFICATE OF CORRECTION

PATENT NO. : 6,328,723 B1
DATED : December 11, 2001
INVENTOR(S) : Burns, Jr. et al.

It is certified that error appears in the above-identified patent and that said Letters Patent is hereby corrected as shown below:

<u>Column 18,</u>
Line 59, after "to" please delete ")" (right parenthesis).

<u>Column 21,</u>
Line 14, please delete "c-5" and insert therefor -- C-5 --.
Line 16, please delete "example" and insert therefor -- Example --.
Line 30, please delete the equation and insert therefor --

$$Z = \frac{N \cdot MS - AS}{\sqrt{\sigma_{AS}^2 + \sigma_{MS}^2}}$$ --

Line 53, please delete the equation and insert therefor --

$$Z = \frac{N \cdot MS - AS}{\sqrt{\sigma_{AS}^2 + \sigma_{MS}^2}}$$ --

<u>Column 22,</u>
Line 42, please delete "extensibilitv" and insert therefor -- extensibility --.
Line 46, please delete "thermnoplastic" and insert therefor -- thermoplastic --.

Signed and Sealed this

Eleventh Day of February, 2003

JAMES E. ROGAN
*Director of the United States Patent and Trademark Office*